United States Patent [19]

Vedder

[11] Patent Number: 5,441,487
[45] Date of Patent: Aug. 15, 1995

[54] PLASTIC NEEDLELESS VALVE HOUSING FOR STANDARD MALE LUER LOCKS

[75] Inventor: Kent B. Vedder, Columbus, Ohio

[73] Assignee: Medex, Inc., Hilliard, Ohio

[21] Appl. No.: 376,969

[22] Filed: Jan. 23, 1995

Related U.S. Application Data

[63] Continuation of Ser. No. 216,669, Mar. 23, 1994, abandoned, which is a continuation-in-part of Ser. No. 160,047, Nov. 30, 1993.

[51] Int. Cl.⁶ ............................................. A61M 39/00
[52] U.S. Cl. ................................. 604/167; 604/169; 604/256
[58] Field of Search .................... 604/30, 91, 167–170, 604/201, 206, 236–237, 247, 256

[56] References Cited

U.S. PATENT DOCUMENTS

| | | |
|---|---|---|
| D. 321,251 | 10/1991 | Jepson et al. . |
| 2,079,692 | 5/1937 | Lapointe . |
| 3,352,531 | 11/1967 | Kilmarx . |
| 3,933,210 | 1/1976 | Skidmore . |
| 3,977,400 | 8/1976 | Moorehead . |
| 3,986,508 | 10/1976 | Barrington . |
| 4,244,607 | 1/1981 | Blose . |
| 4,511,359 | 4/1985 | Vaillancourt . |
| 4,601,703 | 7/1986 | Herlitze . |
| 4,610,665 | 9/1986 | Matsumoto et al. . |
| 4,735,441 | 4/1988 | Setphens . |
| 4,765,588 | 8/1988 | Atkinson . |
| 4,768,568 | 9/1988 | Fournier et al. . |
| 4,857,062 | 8/1989 | Russell . |
| 4,874,377 | 10/1989 | Newgard et al. . |
| 4,886,507 | 12/1989 | Patton et al. . |
| 4,895,346 | 1/1990 | Steigerwald . |
| 4,909,798 | 3/1990 | Fleischhacker et al. . |
| 4,917,668 | 4/1990 | Haindl . |
| 4,950,257 | 8/1990 | Hibbs et al. . |
| 4,966,588 | 10/1990 | Rayman et al. . |
| 5,000,745 | 3/1991 | Guest et al. . |
| 5,006,114 | 4/1991 | Rogers et al. . |
| 5,041,095 | 8/1991 | Littrell . |
| 5,059,186 | 10/1991 | Yamamoto et al. . |
| 5,092,857 | 3/1992 | Fleischhacker . |
| 5,100,394 | 3/1992 | Dudar et al. . |
| 5,104,389 | 4/1992 | Deem et al. . |
| 5,171,234 | 12/1992 | Jepson et al. . |
| 5,188,620 | 2/1993 | Jepson et al. . |
| 5,199,948 | 4/1993 | McPhee . |
| 5,205,775 | 4/1993 | Frank et al. . |
| 5,207,656 | 5/1993 | Kranys . |
| 5,211,634 | 5/1993 | Vaillancourt . |
| 5,215,537 | 6/1993 | Lynn et al. . |
| 5,242,393 | 9/1993 | Brimhall et al. . |
| 5,251,873 | 10/1993 | Atkinson et al. . |
| 5,269,771 | 12/1993 | Thomas et al. . |
| 5,312,377 | 5/1994 | Dalton . |

FOREIGN PATENT DOCUMENTS

| | | |
|---|---|---|
| 0309771 | of 1988 | European Pat. Off. . |
| 3207181 | 5/1983 | Germany . |
| 0111723 | 6/1984 | Germany . |
| 3303718 | 10/1984 | Germany . |
| 8425197 | of 1985 | Germany . |
| 9011103 | 10/1990 | WIPO . |
| 9109643 | 7/1991 | WIPO . |

OTHER PUBLICATIONS

Clave TM brochure/ads (five pages)–believed to have been published and product introduced in early 1993.
International Search Report (PCT/US94/13757) (4 pages).

Primary Examiner—C. Fred Rosenbaum
Assistant Examiner—Perry E. Van Over
Attorney, Agent, or Firm—Wood, Herron & Evans

[57] ABSTRACT

A needleless site (10) includes a slit septum valve (12) held in a plastic housing (20) having a thin-walled cylinder (70) sized to fit inside the lock nut (64) of an ISO male luer lock (54) and a wedging member such as tapered threads (72) to strengthen the cylinder (70) and wedge within lock nut (64) to securely lock male luer lock (54) to site (10). The valve (12) of site (10) is tubular and includes a flange (44) gripped between housing portions (18, 20) having an annular ring (45) digging into the flange.

45 Claims, 2 Drawing Sheets

PLASTIC NEEDLELESS VALVE HOUSING FOR STANDARD MALE LUER LOCKS

RELATED APPLICATION

This is a continuation of Ser. No. 216,669, filed Mar. 23, 1994, abandoned, which is a continuation-in-part of co-pending application Ser. No. 08/160,047, filed Nov. 30, 1993, and assigned to the assignee hereof. The disclosure of aforesaid pending application Ser. No. 08/160,047 is incorporated herein by reference.

BACKGROUND OF THE INVENTION

I. Field of the Invention

The present invention relates to medical valves through which fluid may be injected into or withdrawn from a patient without requiring use of sharp needles, and more specifically, to such valves in plastic housings sized to mate with a standard ISO or ANSI male luer lock.

II. Description of Prior Art

In many medical situations, it is typical to provide a valve, such as a solid rubber septum on a Y-site or a sample site, which is accessible by a needle piercing through the septum in order to introduce fluids into, or remove blood from, a line coupled to a patient's circulatory system via a catheter inserted into the patient such as through the arm. With such needle-piercable valves, the top of the valve is usually adjacent to or at the top of the valve or site housing and so may be readily wiped clean before each use. While this is advantageous for aseptic purposes, the use of sharp needles presents hazards to medical and other personnel due to the risk of needle sticks which could transmit disease.

In order to reduce or eliminate needle stick problems, it has been proposed to replace the needle-piercable rubber septum with a blunt cannula-accessible valve, such as a rubber piece with a slit septum. The slit septum opens under pressure of a blunt cannula thereagainst to allow the blunt cannula to pass into and through the slit and into communication with the fluid line. The most commonly employed blunt cannulas in the medical field are male luer tapers (an example of which is the distal plastic end of a typical syringe). Many male luer tapers are part of a luer lock and thus also have an internally threaded nut or collar associated therewith to securely lock to a female luer cylinder with lock tabs thereon. The dimensions of the locking nut of standard luer locks conform generally to ISO standards thus dictating the size requirements that must be met to mate with a male luer lock. These size requirements have presented difficulty in providing a needleless valve in a plastic housing.

As will be appreciated, it is most desirable to situate the slit septum valve at the top of the valve housing for aseptic purposes. But this requirement has presented an obstacle to housing the valve in such a manner that a male luer lock is usable with that valve. Desirably, plastics are used in the medical field. So it would be advantageous if the valve housing could be entirely of plastic. But, the plastic housing must be thick enough to withstand the various forces it will encounter in use. Unfortunately, the robber valve piece itself requires so much bulk that difficulties have been encountered in providing a plastic housing about the valve that is sturdy and safe, but yet small enough to fit within the nut of the luer lock to be secured thereto. The requirements on the plastic housing, coupled with the minimum size requirements of the slit valve piece, have thus dictated that the overall size of the plastic housing be larger than the internal diameter of the locking nut of a standard ISO or ANSI male luer lock. With such devices, therefore, it has been necessary to use an adaptor having a blunt needle and lock nut sized to fit the valve housing at one end and a standard female luer cylinder with lock tabs at the other end. The adaptor introduces increased costs, and imposes risk of misuse and error in the field.

Another approach would be to provide split luer wings above the top of the valve so that the valve may still be cleaned, yet the male luer lock nut may be securely locked to the valve housing as shown in U.S. Pat. No. 5,203,775, the disclosure of which is incorporated herein by reference. It is desirable, however, to have the locking interaction of the nut and the valve housing occur along the side of the housing at or below the top level of the valve itself. As mentioned above, however, this has not been found to be readily achievable where the valve housing is made of plastic.

One proposal that does shrink the size of the housing so that the housing may fit within the nut to be locked about the sidewall of the valve housing is to use a thin-walled piece of metal, such as a stamped piece of aluminum with lugs projecting from the side thereof, for the housing. However, the rest of the valve housing, especially the portions that mate to the fluid line, will normally be of plastic making the aluminum/plastic valve housing less desirable from a manufacturing standpoint. Also, medical users tend to prefer plastic for a variety of reasons making the metal/plastic valve housing undesirable from a user standpoint as well.

SUMMARY OF THE INVENTION

The present invention provides a blunt cannula-accessible valve, such as a slit septum valve, situated in and at the top of a plastic housing which is sized to lockingly engage a male luer lock nut with the luer taper inserted against or into the valve. To this end, and in accordance with the present invention, the valve is contained within a thin-walled plastic housing or cylinder with the top of the valve at the top opening of the cylinder. The cylinder is sized to fit within the luer lock between the lock nut and the taper with the taper inserted through the valve. Associated with the thin-wall cylinder is a tapered wedging member that is narrow at the top of the cylinder adjacent the top of the valve so that at least the upper edge thereof fits completely within the male luer lock nut between the nut and the luer taper. The tapered wedging member traverses down the sidewall of the cylinder below the top of the valve, and tapers outwardly to increase in diameter as it progresses down the cylinder. The wedging member thus provides strength to the otherwise thin plastic housing wall while at the same time forming a wedge against the internal threads of a male luer lock nut. Consequently, as the male luer taper is inserted into the valve, the luer lock is secured to the valve. The tapered wedging member may be provided by a tapered thread structure, such as a pair of intertwined threads, spirally formed about the thin-wall housing.

By virtue of the foregoing, there is thus provided a needleless valve plastic housing that is sturdy and reliable, yet mates and locks directly to a standard ISO or ANSI male luer lock with the taper thereof inside the valve through the top of the valve at the top of the housing. These and other objects and advantages of the present invention shall be made apparent from the accompanying drawings and description thereof.

BRIEF DESCRIPTION OF THE DRAWINGS

The accompanying drawings, which are incorporated in and constitute a part of this specification, illustrate embodiments of the invention and, together with a general description of the invention given above, and the detailed description given below, serve to explain the principles of the invention.

DETAILED DESCRIPTION OF THE DRAWINGS

Figure 1:
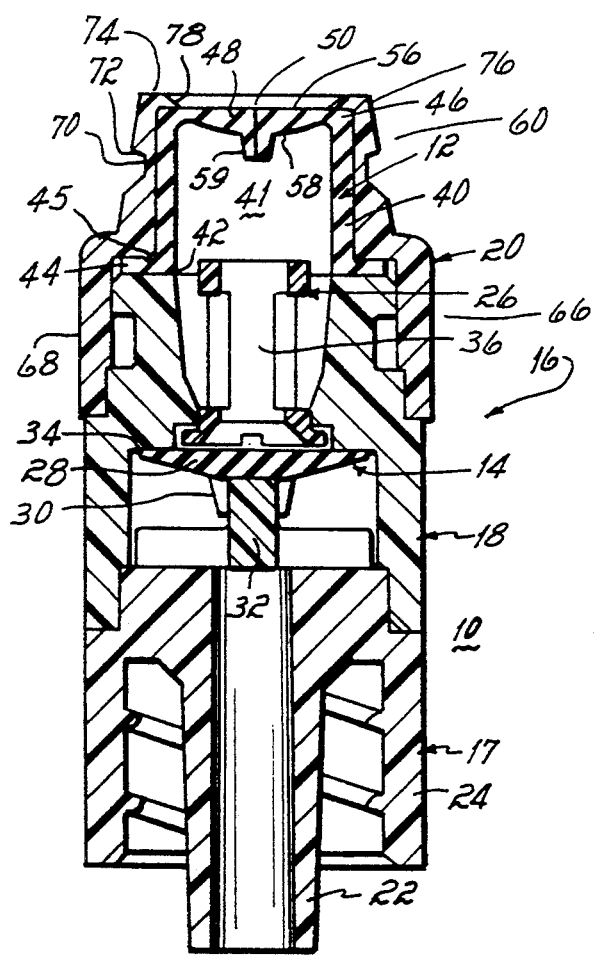
FIG. 1 is a cross-sectional view of a medical site including a needleless valve in a plastic housing incorporating a tapered thread wedging member in accordance with the principles of the present invention.

With reference to FIG. 1, there is shown in cross-section an embodiment of a medical site 10 incorporating the features of the present invention. Site 10 in the embodiment shown here includes a slit septum elastomeric (e.g., silicon or polyisoprene rubber) valve 12 and a disc valve 14 held within plastic (e.g. polycarbonate, Dow Isoplast, rigid PVC, or Ektar) housing 16. Plastic housing 16 includes three portions, namely, male luer lock fluid connector 17, actuator housing 18 and tapered thread housing 20, all bonded together such as with solvent, UV cured adhesive or ultrasonic welding, or they may be frictionally or snap fit together. Connector 17 is a fluid port and includes a standard ISO or ANSI luer taper 22 and locking collar 24 for fluid connection to a fluid line (not shown) coupled, for example, to a patient. Actuator housing 18 contains disk valve 14 comprised of actuator 26 and resilient disc 28, the underside skirt 30 of which is seated on nipple 32 of housing 17 projecting into housing 18. Disc 28 normally bears against valve seat 34 of housing 18 to stay closed but opens under pressure such as from actuator 26 pushed thereagainst. Actuator 26 is open through its interior 36 to permit fluid to flow therethrough and over disc 28 when disc valve 14 is opened. Fluid may then pass out of the lower or outlet end of housing 18 such as via connector 17.

Focusing now on valve 12 and its associate housing 20, valve 12 has a tubular or cylindrical body 40 defining a fluid path 41 therein. Body 40 has an inner diameter of about 0.195 inch and an outer diameter of about 0.246 inch. Extending outwardly about 0.042 inch from the bottom edge 42 of body 40 is an annular lip or flange 44. Actuator housing 18 acts as a support member on which flange 44 sets. Valve housing 20 and actuator housing 18 cooperate to grip valve 12 with flange 44 therebetween. An annular ring 45 is interposed between housing 20 and flange 44. Annular ring 45 may be formed as part of housing 20 and depend therefrom to dig into flange 44 adjacent edge 42 to deform same as seen in FIG. 1. Ring 45 securely holds valve 12 to housing 16 and prevents valve 12 from being extruded inwardly. Ring 45 could, alternatively, be formed on housing 18.

The top edge 46 of body 40 is integrally joined to a closing web 48 to provide an environmental barrier to fluid path 41. To facilitate use of valve 12, a 0.150 inch slit 50 is formed through web 48 to receive a blunt cannula such as male taper 52 of a male luer lock 54, for example (see FIG. 4), into valve 12 through slit 50. Web 48 has a generally flat top 56 and a convex underside 58 and may include structure such as one or more ribs or steps (not shown) to assist in keeping slit 50 in a closed and sealed state until taper 52 bears thereagainst. Extending from underside 58 and along slit 50 may be duckbill lips 59.

Housing 20 is a single injection molded piece and has an upper portion 60 (see FIG. 2) designed to hold tubular body 40 of valve 12 and to mate with the interior threads 62 of locking nut 64 of male luer lock 54. Housing 20 aim includes a lower portion 66 designed to matingly fit over actuator housing 18 to be secured thereto. Lower portion 66 may also be knurled (not shown) about its exterior surface 68 to facilitate handling of site 10 by a user (not shown). Upper portion 60 of housing 20 is sized thin enough to fit into nut 64, yet robust enough to secure to luer lock 54 while protecting valve 12 in normal use. To this end, in accordance with the principles of the present invention, the upper portion 60 of housing 20 may be considered as having two aspects, one being a thin-walled housing cylinder 70 and the other being a wedging member such as a pair of tapered threads 72. Thin-wall cylinder 70 is defined as the cylindrical aspect of housing 20 adjacent and coaxial with tubular body portion 40 of valve 12 and is about 0.012 inch thick. Cylinder 70 has an inner diameter of about 0.246 inch to match to the outer diameter of valve body 40, and an outer diameter of about 0.270 inch. With the thin-wall, it will be appreciated that cylinder 70 is sized to be received into the interior of locking nut 64 of luer lock 54, which has a minimum inner diameter of about 7 mm (0.27 inch). However, cylinder 70 is not itself thick enough to guard valve 12 or withstand even normal use, nor does cylinder 70 itself lock to luer lock 54. The provision of a tapered wedge member such as one or more threads 72 solves these problems.

Figure 2:
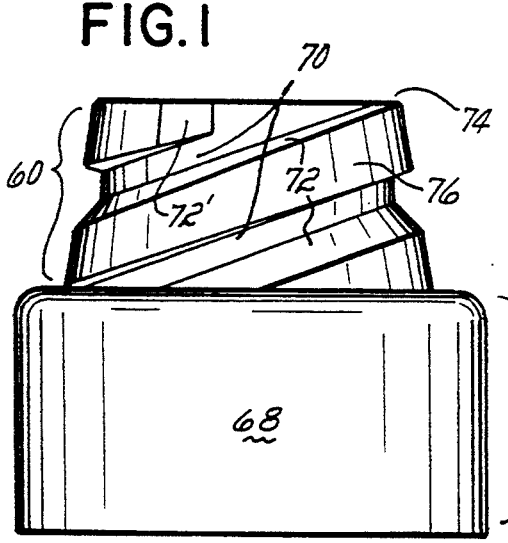
FIG. 2 is a side view of the tapered thread housing of FIG. 1.
Figure 3:
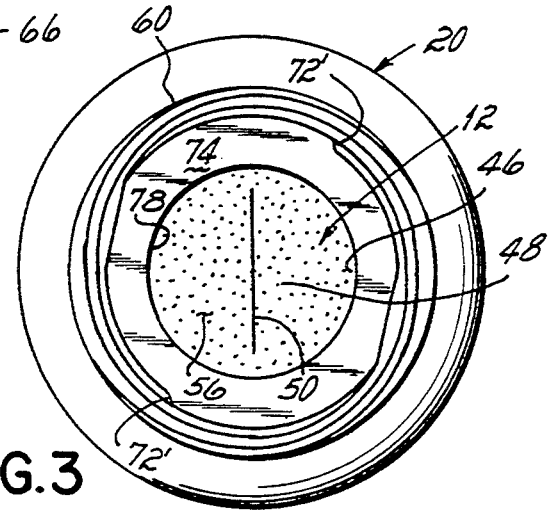
FIG. 3 is a top view of the site of FIG. 1.

With further reference to FIGS. 2 and 3, it may be seen that tapered threads 72 are formed about and spiral downwardly from top end 74 of cylinder 70. The start points 72' of the threads 72 are on opposite sides of cylinder 70 so that threads 72 intertwine as seen in FIG. 3. Cylinder 70 defines the minor diameter of threads 72 and the distal or outer edge 76 of each thread 72 defines the major diameter thereof. The major diameter 76 extends radially outwardly of cylinder 70 only slightly (about 0.008 inch) at top end 74 and is thus narrow at the top end 74 of cylinder 70, to be sized to still be received within the interior of locking nut 64. As threads 72 progress spirally downwardly towards lower portion 66, the major diameter 76 increases in thickness to about 0.036 inch such that the outer diameter thereof is larger than the inner diameter of lock nut 64. Thus, at the lower end of threads 72 spaced from top end 74, the threads are wider than at top end 74. Threads 72 are 10 pitch with double start and cylinder 70 is about 0.171 inch long or tall to be coextensive with tubular body 40 of valve 12 such that the top 56 of slit web 48 is at or generally flush with opening 70 at top end 74 of housing 20 (and cylinder 70) to be aseptically cleaned by wiping thereacross. Top end 74 of housing 12 defines a lip projecting inwardly from cylinder 70 about 0.023 inch to overlie top edge 46 of valve 12 and help hold valve 12 in place with the top surface 56 thereof generally flush with housing top end 74. Top surface 56 is thus accessible via inlet opening 78 of cylinder 70 to be cleaned with a gauze pad (not shown), for example, wiped thereacross.

It will be appreciated that the tapered threads 72 are integral with cylinder 70 and function to strengthen cylinder 70 without making housing 20 too large to mate with lock nut 154, yet provide a positive and gradual locking function between site 10 and luer lock 54. These functions are thus provided in a plastic housing for a needleless valve which is surfaced at the top of the valve housing for aseptic purposes, but which is lockingly receivable into a standard ISO or ANSI male luer lock.

Figure 4:
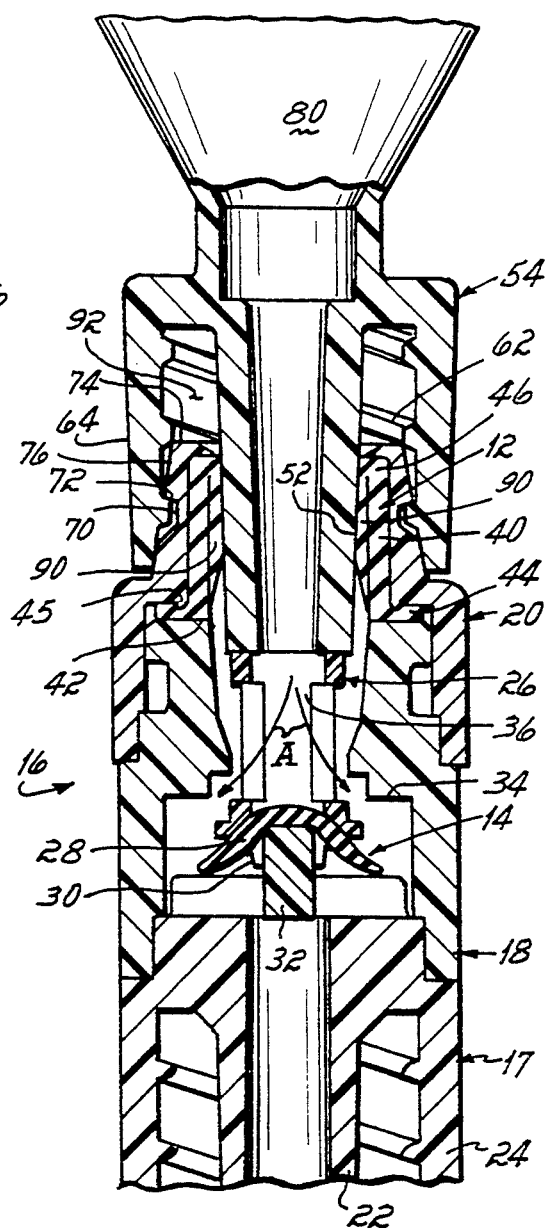
FIG. 4 is a cross-sectional view of the site of FIG. 1 with a standard ISO or ANSI male luer lock attached thereto for purposes of explaining the principles of the present invention.

In use, flat top 56 of web 48 is wiped clean and, as seen in FIG. 4, taper 52 of luer lock 54 (luer lock 54 could be part of a syringe 80 as is well known) is inserted into and through slit 50 of web 48. As that occurs, the top end 74 of upper portion 60 of housing 20 is received into the interior of locking nut 154. Nut 64 is rotated as it passes over top end 74. Threads 62 of luer lock 54 and tapered thread 72 of housing 20 cooperate to draw taper 52 into actuator housing 18. Taper 52 then passes into fluid path 41 and impacts against actuator 26 moving it downwardly into disc 28 to thereby open same for fluid to flow through taper 52 and actuator 26, over disc 28 and through luer taper 22 of connector 17 along the path of Arrows A (or vice versa) to complete a fluid connection through site 10. Also, the portions of web 48 to either side of slit 50 flex downwardly and outwardly to either side of taper 52 like lips, as at 90 in FIG. 4. At the same time, lock nut 64 does not merely threadably engage to housing 20 as would be typically expected, but instead is wedged thereagainst by coaction of the material of plastic housing upper portion 60, and particularly tapered threads 72, and the major diameter 92 of locking collar 64 to thereby securely hold male luer lock 54 to site 10. Luer lock 54 may be easily removed by reverse rotation of locking collar 64 to thereby release the wedge and remove taper 54 which also recloses disc valve 14 and slit septum valve 12.

Figure 5:
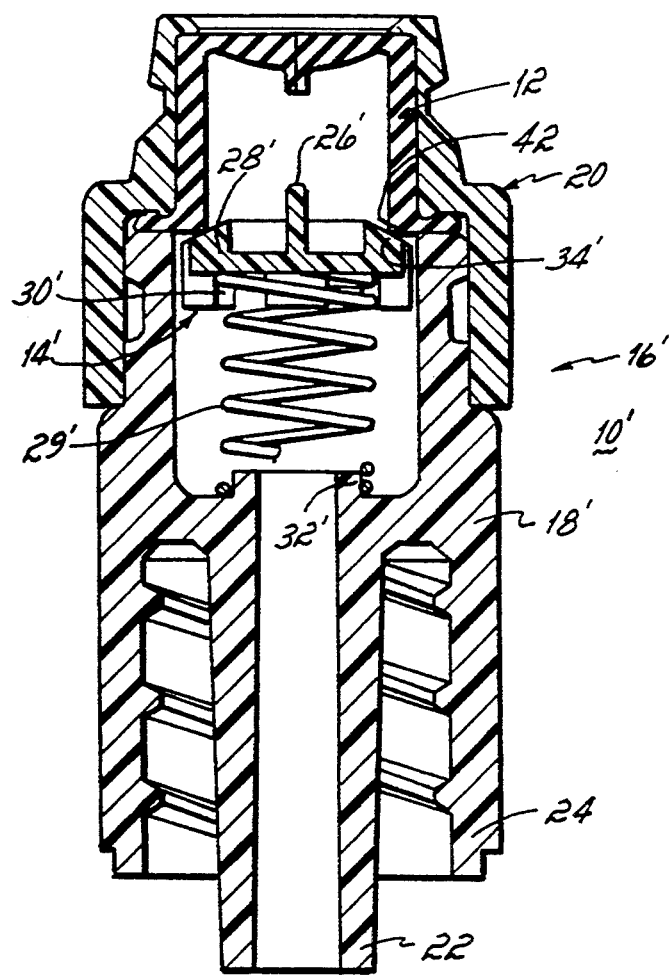
FIG. 5 is a cross-sectional view of another medical site including the tapered thread housing of FIG. 1.

With reference to FIG. 5, another site 10' is shown including the tapered thread housing 20 as in the case of site 10 of FIG. 1. To this end, site 10' of FIG. 5 includes valve 12 and thread housing 20 as abovedescribed. However, connector 17 and actuator housing 18 are combined into one housing piece 18' to support spring-biased disc valve 14'. Disc valve 14' includes a plastic disc 28' which is biased closed by spring 29' against valve seat 34' defined at the lower edge 42 of valve 12. Spring 29' seats over mouth 32' of housing 18' and within a groove 30' defined under disc 28'. Extending up from disc 28' is actuator piece 26' to cooperate with taper 52 passed through valve 12 to push disc 28' away from valve seat 34' to permit fluid communication through housing 16' similar to that in the case of site 10 of FIG. 1.

While the present invention has been illustrated by the description of an embodiment thereof, and while the embodiment has been described in considerable detail, it is not intended to restrict or in any way limit the scope of the appended claims to such detail. Additional advantages and modifications will readily appear to those skilled in the art. For example, the secondary or check valve of the site of aforementioned parent application Ser. No. 08/160,047 could be disc valve 14 as described herein. Additionally, the fluid port of connector 17 could instead be provided by a Y-site or T-shaped sample or injection site, or a tubing port, as will be readily appreciated. Additionally, instead of the major diameter 76 of the wedging member tapering outwardly, that outer surface could be held at a fixed diameter with the minor diameter of threads 72 tapering outwardly instead. Or both the minor and major diameters of thread(s) 72 could taper outwardly. Further, the thread tapering could be in discrete portions of the overall thread length or the threads may be truncated and traverse only partway down cylinder 70. In any event, the top end must fit completely within the locking collar and the lower end must be sized to wedge against the internal threads (major and/or minor diameters) of the locking collar. Moreover, although the wedging member is described as a thread structure or pair of threads, a single thread or other tapered wedging member structure may be employed to functionally thicken or strengthen cylinder 70 and also lock within luer lock 54. Alternatively, where the primary concern is to strengthen the housing, the major and minor diameters could be uniform, i.e., non-tapered, such as a thread chased down a cylinder. The invention in its broader aspects is therefore not limited to the specific details, representative apparatus and method and illustrative examples shown and described. Accordingly, departures may be made from such details without departing from the scope or spirit of applicant's general inventive concept.

Having described the invention, what is claimed is:

1. In a medical device for coupling to a standard male luer lock having a luer taper and an internally threaded locking nut thereabout wherein the medical device includes a normally-closed valve being openable by the taper of the male luer lock, the improvement comprising:

a plastic housing surrounding the valve and having an opening sized to receive the luer taper therethrough, a top surface of the valve being situated at the opening of the housing, the housing including a tapered exterior surface which is (i) narrow adjacent the opening and sized to be received into the interior of the locking nut of the male luer lock, and (ii) wider spaced from the opening such that the tapered exterior surface wedgingly interacts with the interior of the locking nut of the male luer lock to hold the male luer lock to the device with the valve opened by the luer taper.

2. In the medical device of claim 1 wherein the housing further includes a thread extending thereabout.

3. In the medical device of claim 2, a portion of the tapered exterior surface being defined by the thread.

4. In the medical device of claim 2 wherein the thread extends from adjacent the housing opening.

5. In the medical device of claim 4 wherein the thread is truncated.

6. In the medical device of claim 2 wherein the thread extends along the tapered exterior surface and has a major diameter and a minor diameter, at least one of the major and minor diameters being tapered so as to be narrow adjacent the opening and wider spaced from the opening.

7. In the medical device of claim 6 wherein only the major diameter is tapered.

8. In the medical device of claim 1 wherein the valve includes an annular flange, the medical device further having a support member cooperating with the housing to grip the valve flange, the improvement further comprising a depending annular ring formed on the housing and situated to engage the flange.

9. In a medical device for coupling to a standard male luer lock having a luer taper and an internally threaded locking nut thereabout wherein the medical device includes a normally-closed valve being openable by the taper of the male luer lock, the improvement comprising:
   a plastic housing surrounding the valve and having an opening sized to receive the luer taper therethrough, a top surface of the valve being situated at the opening of the housing, the housing including a portion having an upper end adjacent the opening and a lower end spaced from the opening;
   a thread extending about the upper end;
   the lower end being connected to the upper end by a tapered exterior surface which is (i) narrow adjacent the upper end and sized to be received into the interior of the locking nut of the male luer lock, and (ii) wider adjacent the lower end such that the tapered exterior surface wedgingly interacts with the interior of the locking nut of the male luer lock to hold the male luer lock to the device with the valve opened by the luer taper.

10. In the medical device of claim 9 wherein the thread extends from about the opening and toward the lower end.

11. In the medical device of claim 10 wherein the thread extends along the tapered exterior surface.

12. In the medical device of claim 11 wherein the thread extends completely to the lower end.

13. In the medical device of claim 12 wherein the thread is in discrete portions.

14. In the medical device of claim 11 wherein the thread is truncated.

15. In the medical device of claim 10 wherein the thread has a major diameter and a minor diameter, at lease one of the major and minor diameters being tapered so as to be narrow adjacent the upper end and wider spaced from the upper end.

16. In a medical device for coupling to a standard male luer lock having a luer taper and an internally threaded locking nut thereabout wherein the medical device includes a normally-closed slit septum valve being openable under pressure of the taper of the male luer lock thereagainst, the improvement comprising:
   a thin-walled plastic cylinder surrounding the valve and having an outer diameter sized to be received into the interior of the locking nut of the male luer lock, the cylinder having an opening With the slit septum being situated at the opening of the cylinder; and
   a plastic tapered thread extending about the plastic cylinder, the thread having (i) a narrow end adjacent the cylinder opening sized to be received into the interior of the locking nut of the male luer lock, and (ii) a wider end spaced from the cylinder opening such that the thread strengthens the cylinder and interacts with the internal threads of the locking nut of the male luer lock to lock the male luer lock to the device with the valve opened by the luer taper inserted into the slit septum.

17. In the medical device of claim 16 wherein the cylinder and thread are integrally formed as a single piece.

18. In the medical device of claim 16 wherein the valve is held by a housing, the cylinder defining a portion of the housing.

19. In the medical device of claim 18 wherein the cylinder and thread are integrally formed as a single piece.

20. In the medical device of claim 18 wherein the valve includes an annular flange, the medical device further having a support member cooperating with the housing to grip the valve flange, the improvement further comprising a depending annular ring formed on the housing and situated to engage the flange.

21. In the medical device of claim 16, the improvement further comprising a second thread extending about the plastic cylinder and intertwined with the tapered thread.

22. In the medical device of claim 21, the second thread being tapered and having (i) a narrow end adjacent the cylinder opening sized to be received into the interior of the locking nut of the male luer lock, and (ii) a wider end spaced from the cylinder opening such that the tapered and second thread cooperate to strengthen the cylinder and interact with the internal threads of the locking nut of the male luer lock to lock the male luer lock to the device with the valve opened by the luer taper inserted into the slit septum.

23. In the medical device of claim 22 wherein the cylinder and threads are integrally formed as a single piece.

24. In a medical device for coupling to a standard male luer lock having a luer taper and an internally threaded locking nut thereabout wherein the medical device includes a normally-closed valve being openable under pressure of the taper of the male luer lock thereagainst, the improvement comprising:
   a thin-walled plastic cylinder surrounding the valve and having an outer diameter sized to be received into the interior of the locking nut of the male luer lock, the cylinder having an opening with a top surface of the valve being situated at the opening of the cylinder; and
   a tapered wedging member extending about the plastic cylinder, the wedging member having (i) a narrow end adjacent the cylinder opening sized to be received into the interior of the locking nut of the male luer lock, and (ii) a wider end spaced from the cylinder opening such that the wedging member strengthens the cylinder and interacts with the internal threads of the locking nut of the male luer lock to lock the male luer lock to the device with the valve opened by the luer taper.

25. In the medical device of claim 24 wherein the wedging member is comprised of plastic.

26. In the medical device of claim 25 wherein the cylinder and wedging member are integrally formed as a single piece.

27. In the medical device of claim 24 wherein the valve is held by a housing, the cylinder defining a portion of the housing.

28. In the medical device of claim 27 wherein the cylinder and wedging member are integrally formed as one piece.

29. In the medical device of claim 27 wherein the valve includes an annular flange, the medical device further having a support member cooperating with the housing to grip the valve flange, the improvement further comprising a depending annular ring formed on the housing and situated to engage the flange.

30. In the medical device of claim 24 wherein the tapered wedging member includes a thread having a major diameter and a minor diameter, at least one of the major and minor diameters being tapered so as to be narrow adjacent the cylinder opening and wider spaced from the cylinder opening.

31. In the medical device of claim 30 wherein only the major diameter is tapered.

32. In the medical device of claim 24 wherein the improvement comprises a pair of said tapered wedging members each having (i) a narrow end adjacent the cylinder opening sized to be received into the interior of the locking nut of the male luer lock, and (ii) a wider end spaced from the cylinder opening such that the wedging members strengthen the cylinder and interact with the internal threads of the locking nut of the male luer lock to lock the male luer lock to the device with the valve opened by the luer taper.

33. In a medical device for coupling to a standard male luer lock having a luer taper and an internally threaded locking nut thereabout wherein the medical device includes a normally-closed valve being openable under pressure of the taper of the male luer lock thereagainst, the improvement comprising:

a thin-walled plastic cylinder surrounding the valve and having an outer diameter sized to be received into the interior of the locking nut of the male luer lock, the cylinder having an opening with a top surface of the valve being situated at the opening of the cylinder; and a thread spiraling along the cylinder and away from the cylinder opening, the thread being sized to strengthen the cylinder and interact with the internal threads of the locking nut of the male luer lock.

34. In the device of claim 33 wherein the thread is comprised of plastic.

35. In the device of claim 34 wherein the cylinder and thread are integrally formed as a single piece.

36. In the medical device of claim 33 wherein the valve is held by a housing, the cylinder defining a portion of the housing.

37. In the device of claim 36 wherein the thread is comprised of plastic.

38. In the device of claim 37 wherein the cylinder and thread are integrally formed as a single piece.

39. In the medical device of claim 36 wherein the valve includes an annular flange, the medical device further having a support member cooperating with the housing to grip the valve flange, the improvement further comprising a depending annular ring formed on the housing and situated to engage the flange.

40. In the medical device of claim 33 wherein the thread includes a major diameter and a minor diameter, at least one of the major and minor diameters being tapered so as to be narrow adjacent the cylinder opening and wider spaced from the cylinder opening.

41. In the medical device of claim 40 wherein only the major diameter is tapered.

42. In a medical device for coupling to a male luer taper wherein the medical device includes a normally-closed elastomeric valve having a tubular body and an annular flange extending outwardly of the tubular body, the valve being openable under pressure of the taper thereagainst, the improvement comprising:

a plastic housing surrounding the valve, the housing having first and second portions, the flange being situated between the housing first and second portions whereby to grip the valve; and an annular ring interposed between the flange and one of the housing portions situated to dig into the flange.

43. In the medical device of claim 42, the ring being formed as part of one of the housing portions.

44. In the medical device of claim 42 wherein the first housing portion surrounds the tubular body of the valve, the ring being interposed between the first housing portion and the flange.

45. In the medical device of claim 44 wherein the ring is formed as part of the first housing portion.

* * * * *